(12) United States Patent
Friesen et al.

(10) Patent No.: US 8,377,904 B2
(45) Date of Patent: Feb. 19, 2013

(54) COMPOSITION AND METHOD FOR USE IN CARTILAGE AFFECTING CONDITIONS

(75) Inventors: Kim Gene Friesen, Topeka, KS (US); Philip William Toll, Valley Falls, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 179 days.

(21) Appl. No.: 11/199,350

(22) Filed: Aug. 8, 2005

(65) Prior Publication Data

US 2006/0073192 A1    Apr. 6, 2006

Related U.S. Application Data

(63) Continuation-in-part of application No. 10/774,781, filed on Feb. 9, 2004, now abandoned.

(51) Int. Cl.
*A01N 43/04*   (2006.01)
*A01N 55/04*   (2006.01)
*A61K 31/32*   (2006.01)
*A01N 37/12*   (2006.01)

(52) U.S. Cl. ............................ 514/47; 514/492; 514/562
(58) Field of Classification Search .................... 514/47, 514/492, 562
See application file for complete search history.

(56) References Cited

U.S. PATENT DOCUMENTS

| | | | | |
|---|---|---|---|---|
| 3,965,268 A | * | 6/1976 | Stocker et al. | 426/331 |
| 4,282,254 A | * | 8/1981 | Franzen et al. | 426/2 |
| 4,374,135 A | * | 2/1983 | Johnson | 514/218 |
| 4,804,745 A | | 2/1989 | Koepff et al. | |
| 5,053,429 A | * | 10/1991 | Hirsch et al. | 514/562 |
| 5,364,845 A | | 11/1994 | Henderson | |
| 5,385,887 A | * | 1/1995 | Yim et al. | 514/12 |
| 5,587,363 A | | 12/1996 | Henderson | |
| 5,840,715 A | * | 11/1998 | Florio | 514/62 |
| 5,952,367 A | | 9/1999 | Pak | |
| 6,255,295 B1 | * | 7/2001 | Henderson et al. | 514/54 |
| 6,271,213 B1 | | 8/2001 | Henderson et al. | |
| 6,451,771 B1 | | 9/2002 | Henderson et al. | |
| 6,492,349 B1 | | 12/2002 | Henderson | |
| 6,911,215 B2 | * | 6/2005 | Myers | 424/439 |
| 2002/0182276 A1 | * | 12/2002 | Wadsworth et al. | 424/765 |
| 2003/0224071 A1 | | 12/2003 | Murad | |

FOREIGN PATENT DOCUMENTS

| WO | WO 98/48816 A1 | 11/1998 |
|---|---|---|
| WO | WO 99/003365 | 1/1999 |
| WO | WO 99/62524 | 12/1999 |
| WO | WO 03/057201 A2 | 7/2003 |
| WO | WO 03/084346 | 10/2003 |
| WO | WO 2005006877 * | 1/2005 |
| WO | WO 2005/077386 A1 | 8/2005 |
| WO | WO 2006/074089 A2 | 7/2006 |

OTHER PUBLICATIONS www.dhea.com/jointrec.htm (1998).*
www.deaconess.com (pp. 1-31).*
http://www.icewindfarm.com/nuvet.html, Dec. 2002, 7 pages.*
Life Extension, http://www.lef.org (1995), 2 pages.*
Medical Management of Osteoarthritis Gdhfa.org (1997), 2 pages.*
Database WPI Section Ch, Week 200102 Derwent Publications Ltd., London, GB; Class B05, AN 2001-016556 XP002325863 & ZA 9 905 557 A (Log-Negentien Beleggings Pty Ltd) Jun. 28, 2000.
Gaby A R: "Natural Treatments for Osteoarthritis" Alternative Medicine Review, Thorne Research Inc., Sandpoint, US, vol. 4, No. 5, 1999, pp. 330-341, XP000992206 ISSN: 1089-5159.
McLaughlin R: "Management of Chronic Osteoarthritic Pain" Veterinary Clinics of North America: Small Animal Practice, Saunders, Philadelphia, US, vol. 30, No. 4, Jul. 2000, pp. 933-949, XP000991455 ISSN:0195-5616.
International Search Report and Written Opinion for PCT/US2005/004274 filed on Feb. 9, 2005.
Adam et al., 1998, "May Collagen Hydrolysate Rich Diet (CHRD) Extend the Effect of Calcitonin in Postmenopausal Osteoporosis?" Connective Tissue Diseases XVII:25-36.
Beren et al., 2001, "Effect of pre-loading oral glucosamine HCI/chondroitin sultate/manganese ascorbate combination on experimental arthritis in rats," Experimental Biology and Medicine (Maywood, NJ) 226(2):144-151.
Byron et al., 2003, "Influence of glucosamine on matrix metalloproteinase expression and activity in lipopolysaccharide-stimulated equine chondrocytes," American J. Veterinary Research 64(6):666-671.
Fabiani et al., 2001, "Antioxidants prevent the lymphocyte DNA damage induced by PMA-stimulated monocytes," Nutrition and Cancer 39(2):284-291.
Hardie et al., 2002, "Radiographic evidence of degenerative joint disease in geriatric cats: 100 cases (1994-1997)," J. American Veterinary Medical Association 220(5):628-632.
Hardy et al., 2002, "S-Adenosyl-L-Methionine for Treatment of Depression, Osteoarthritis, and Liver Disease," Evidence Report/Technology Assessment No. 64. (Prepared by Southern California Evidence-based Practice Center under Contract No. 290-97-0001.) AHRQ Publication No. 02-E034 Rockville, MD: Agency for Healthcare Research and Quality.
International Search Report and Written Opinion in International Application No. PCT/US06/031071, mailed Mar. 23, 2007.
Johnston, 1997, "Osteoarthritis. Joint anatomy, physiology, and pathobiology," Vet. Clinics of N. America: Small Animal Practice 27(4):699-720.
Kroger et al., 1999, "The effect of tryptophan plus methionine, 5-azacytidine, and methotrexate on adjuvant arthritis of rat," General Pharmacology 33(2):195-201.
Martinez et al., 1997, "Acquired conditions that lead to osteoarthritis in the dog," Vet. Clinics of N. America: Small Animal Practice 27(4):759-775.
Oesser et al., 1999, "Oral administration of (14)C labeled gelatin hydrolysate leads to an accumulation of radioactivity in cartilage of mice (C57/BL)," J. Nutrition 129(10):1891-1895.
Soeken et al., 2002, "Safety and efficacy of S-adenosylmethionine (SAMe) for osteoarthritis," J. Family Practice 51(5):425-430.

(Continued)

*Primary Examiner* — Shirley V Gembeh
(74) *Attorney, Agent, or Firm* — Shannon McGarrah

(57) ABSTRACT

A method for decreasing cartilage abnormalities and preventing cartilage degradation in an animal using a combination at least one sulfur containing amino acid and manganese.

28 Claims, No Drawings

OTHER PUBLICATIONS

Takizawa et al., 2000, "Production of tissue inhibitor of metalloproteinases 3 is selectively enhanced by calcium pentosan polysulfate in human rheumatoid synovial fibroblasts," Arthritis Rheumatism 43(4):812-820.

Yen et al., 2003, "Manganese superoxide dismutase and cytochrome P450 1A1 genes polymorphisms in rheumatoid arthritis in Taiwan," Human Immunology 64(3):366-373.

* cited by examiner

COMPOSITION AND METHOD FOR USE IN CARTILAGE AFFECTING CONDITIONS

CROSS-REFERENCE TO RELATED APPLICATIONS

This application is a continuation-in-part of U.S. patent application Ser. No. 10/774,781 filed on Feb. 9, 2004 now abandoned. This application claims the benefit to PCT Application No. PCT/US05/04274 filed on Feb. 9, 2005. The above applications are incorporated herein by reference in their entirety.

BACKGROUND OF THE INVENTION

1. Field of the Invention

This invention relates generally to compositions and methods for improving joint health in animals and particularly to the use of sulfur containing amino acids and manganese to decreasing cartilage abnormalities in animals.

2. Description of the Prior Art

Virtually all joints have cartilage. Cartilage is important in the body of animals for providing flexibility, compressibility under pressure, cushion, tensile strength, range of motion and smoothness of movement within joints. Examples of joints having cartilage include fingers and toes, neck, knee, hip, shoulder and the like. Animals can suffer from a number of conditions where cartilage is negatively affected thereby bringing about a reduction in the joint's flexibility, compressibility and often times resulting in a generalized inflammation of the joint and/or tissue surrounding the joints. Such animal then has significant loss of joint function and experiences pain.

U.S. Pat. No. 5,587,363 to Henderson proposes a composition for protection, treatment and repair of connective tissues in humans and animals and a method for the treatment of connective tissues in humans and animals by the administration of the composition. The composition includes amino sugars and glycosaminoglycans. U.S. Pat. No. 6,255,295 to Henderson proposes a composition for protection, treatment and repair and reducing the inflammation of connective tissues in mammals and the method for protection treatment and repair of connective tissues in mammals by the administration of the composition. The composition includes at least two compounds selected from s-adenosylmethionine, an amino sugar, and glycosoaminoglycan-like compound. The composition optionally includes manganese and the composition also optionally includes methyl donors and methyl donor cofactors. U.S. Pat. No. 6,271,213 to Henderson proposes a composition for protection, treatment and repair and reducing the inflammation of connective tissues in mammals and the method for protection treatment and repair of connective tissues in mammals by the administration of the composition. The composition includes at least two compounds selected from s-adenosylmethionine, an amino sugar, and glycosoaminoglycan-like compound. The composition optionally includes manganese and the composition also optionally includes methyl donors and methyl donor cofactors. U.S. Pat. No. 5,952,367 to Pak proposes a method of treating pain caused by tendonitis, arthritis and the like comprises administering the effective amount of a non-steroidal anti-inflammatory drug and ingesting an amount of methionine and a sugar in combination.

Kroger et al. (1999) the Effect of Tryptophan plus Methionine-5-Azazytidine and Methotrexate on Adjuvant Arthritis of Rat; Gen. Pharm. 33:195-201 report a treatment with combination of tryptophan and methionine alone stimulate arthritic reactions. However, treatment with the two drugs 5-azazytidine and methotrexate in combination with tryptophan and methionine clearly reduced development of the adjuvant arthritis and this effect is stronger than either the 5-azazytidine or methotrexate alone. Agency for Health Care Research and Quality (2002) Evidence Report Technology Assessment No. 64 report that studies were identified in the literature that included a meta analysis of the efficiency of S-adenosyl-L methionine (SAMe) to decrease the pain of osteoarthritis. Results show that when compared with non-steroidal anti-inflammatory medication, treatment with SAMe was not associated with statistically significant difference in outcomes. However, one randomized clinical trial showed an effective size in favor of SAMe of 0.20 compared to a placebo, thus, indicating a decrease in the pain of osteoarthritis. Johnston (1997), Orthoarthritis. Veterinary Clinics of North America; Small Animal Practice 27:699-720 reports that osteoarthritis is a slow progressive disorder of synovial joints that affects about 20% of the canine population over one year of age. This joint disorder is characterized by the loss of balance between synthesis and degradation of articular cartilage constituents leading to subsequent erosion of joint cartilage, remodeling of underlying bone, osteophyte formation and variable degrees of synovitis. Martinez et al. (1997) Acquired conditions that lead to osteoarthritis in a dog. Veterinary Clinics of North America: Small Animal Practice; 27:759-775 report that some of the most common causes of secondary osteoarthritis seen in companion animals are anterior cruciate ligament rupture, osteochrondritis dissecans, fragmented coronoid process and hip dysplasia. Other examples of cartilage affected conditions include but are not limited to osteochondrosis, synovitis, bacteria purulent arthritis, osteoarthropathia psoriatica, subchondrial cystic lesions, physitis, angular limb deformities and cuboidal bone malformation.

Most large dogs develop arthritis as they age. Large dog breeds are more susceptible to arthritis due to their increased mass and/or genetic disposition. Large dogs are not the only animals at risk of arthritis and other cartilage conditions. Hardie et al. (2002) Radiographic evidence of degenerative joint disease in geriatric cats. JAVMA 220(5):628-632 report that arthritis and other degenerative joint diseases have been commonly recognized in dogs and such conditions have been shown to be prevalent in cats. Other animals at risk of developing cartilage affecting conditions include, but are not limited to, mammals such as canine, feline, equine, hicrine, ovine, porcine, bovine, human and non-human primate species, and birds including turkeys and chickens.

Known methods for decreasing cartilage abnormalities in an animal have limited efficacy. There is, therefore, a need for new methods and compositions for treating, preventing, or improving such conditions in animals.

SUMMARY OF THE INVENTION

The present invention provides compositions and methods for improving joint health. Thus, various embodiments provide methods for decreasing cartilage abnormalities in an animal comprising administering to the animal an effective amount of a combination of at least one sulfur containing amino acid and manganese.

Various embodiments provide methods for preventing degradation of cartilage tissue in an animal comprising administering to the animal an effective amount of a combination of at least one sulfur containing amino acid and manganese.

Various embodiments provide compositions suitable for systemic administration to an animal comprising a cartilage abnormality decreasing or a cartilage abnormality preventing effective amount of a combination of at least one sulfur containing amino acid and manganese. Various embodiments provide foods that comprise a combination of at least one sulfur containing amino acid and manganese in an amount effective to improve the animal's joint health.

Further areas of applicability of the various embodiments will become apparent from the detailed description provided hereinafter.

DETAILED DESCRIPTION OF THE INVENTION

The various embodiments provide compositions and methods for improving joint health in animals and in particular in companion animals such as dogs and cats. The description of specific examples, while indicating various embodiments, are intended for purposes of illustration only and are not intended to limit the scope of the various embodiments. Moreover, recitation of multiple embodiments of the stated features is not intended to exclude other embodiments having additional features, or other embodiments incorporating different combinations of the stated features.

All literature and similar materials cited in this application, including but not limited to, patents, patent applications, articles, books, treatises, and internet web pages, regardless of the format of such literature and similar materials, are expressly incorporated by reference in their entirety for any purpose to the extent allowed by law. In the event that one or more of the incorporated literature and similar materials differs from or contradicts this application, including but not limited to defined terms, term usage, described techniques, or the like, this application controls.

Cartilage is made up of living tissue that is continually broken down and replaced. However, injury, stress on joints and the aging process can harm cartilage tissue, often without any obvious signals until a lot of damage has been done. Cartilage is a substance that is made up of 65%-80% water. The remaining portion is made up of three other components, collagen, chondrocytes and proteoglycans. Collagen gives the cartilage its shock absorption and elasticity, whereas proteoglycans are larger molecules that give cartilage its ability to stretch and then bounce back in response to movements. However, as with all things, collagen and proteoglycans age. Chondrocytes clean away aged proteoglycans and collagen and produce new ones. These components, along with water, work together to ensure cartilage is healthy, smooth, and pain free movement in joints. When any one of these components declines, cartilage can deteriorate and osteoarthritis will begin to develop.

Osteoarthritis affects predominately joint cartilage, the smooth glistening surface that lines the bone within the joint. The function of the cartilage is to provide shock absorbency and reduce friction as the joint glides. Osteoarthritis produces thinning and damage to the cartilage, which will break down becoming rough and eroded. Cartilage and bone are further damaged as the bones rub together and deformity results when one side of the joint collapses more than the other side. When the cartilage loss is great, there may be severe pain in the involved joint with use or even at rest.

Various substances have been used in attempts to improve such conditions as described above. Such attempts have included using glucosamine, chondroitin and chondroitin sulfate supplements in the treatment of arthritis. Glucosamine is a component of proteoglycans, which maintain fluid in the cartilage. Chondroitin is another component of proteoglycans. *Perna canaliculata* is a rich source of glycosaminoglycans (GAGs). Unfortunately, these GAGs are poorly absorbed when taken by mouth. *Perna* may be beneficial for the treatment of arthritis, but the observed benefits may be more from its natural anti-inflammatory effect than from direct absorption of glycosaminoglycans. Creatine plays an important role in the conversion of glucose into muscular energy and may have value in improving muscular strength and making older animals feel more energetic. Methylsulfonylmethane (MSM) has an anti-inflammatory effect that slows the progression of arthritis and relieves pain. Of course, other substances typically used by humans but may also be used in treatment of non-human animals include aspirin, anti-inflammatories such as ibuprofen, COX-2 inhibitors and other medicinal and pharmaceutical compositions.

In various embodiments, compositions and methods to improve, treat, prevent and/or alleviate the above described conditions include the administration to an animal of a combination of at least one sulfur containing amino acid and manganese.

The term "sulfur containing amino acid(s)" means sulfur containing amino acid and their derivitives. The term "managing a cartilage condition" means to improve, treat, prevent and/or alleviate at least one cartilage affected condition and/or to provide a positive cartilage effect to an animal. The term "managing a cartilage condition" includes preventative methods for an animal with a latent cartilage effecting condition, a predisposition, whether hereditary or otherwise to a cartilage affected condition or as a preventative measure at any time during an animal's lifetime to strengthen cartilage, prevent abnormalities in cartilage, improve joint health, decrease the effects of joint degradation over age, or to prevent arthritis or other joint affected conditions. Illustrative examples of a positive cartilage effect includes increasing flexibility, repairing lesions, reducing inflammation, improving mobility, strengthening cartilage, reducing abnormalities, and/or preventing any of reduced flexibility and/or mobility, weakening and/or degrading cartilage, abnormalities and/or lesions, inflammation, or a cartilage affected condition, and the like. Illustrative examples of such cartilage affected conditions include osteoarthritis, rheumatoid arthritis, osteochondrosis, degenerative joint disease, synovitis, bacterial purulent arthritis, osteoarthropathia psoriatica and the like.

The animal can be human or non-human. In various embodiments, the animal may be a vertebrate, for example a fish, a bird, a reptile or a mammal. Illustratively among mammals, the animal can be a member of the order Carnivora, including without limitation canine and feline species. In various embodiments, the animal may be a companion animal. A "companion animal" herein is an individual animal of any species kept by a human caregiver as a pet, or any individual animal of a variety of species that have been widely domesticated as pets, including dogs (*Canis familiaris*) and cats (*Felis domesticus*), whether or not the individual animal is kept solely or partly for companionship. Thus "companion animals" herein include working dogs, farm cats kept for rodent control, etc., as well as pet dogs and cats.

Notwithstanding these various embodiments, it will be understood that the methods also are generally suitable for other mammals, including non-human mammals such as non-human primates (e.g., monkeys, chimpanzees, etc.), companion and working animals (e.g., horses, etc.), farm animals (e.g., goats, sheep, swine, cattle, etc.), and wild and zoo animals (e.g., wolves, bears, deer, lions, tigers, giraffes, elephants, etc.). Various embodiments also are generally suitable for use with non-mammalian animals, such as companion, farm, zoo, and wild birds, (including, for example, song birds, parrots, ducks, geese, chickens, turkeys, ostriches, etc.).

The term "diet", as used herein, means the food and drink regularly consumed by the animal and may include a daily ration provided by a care giver. A daily ration may include any suitable food composition that provides adequate nutrition for the animal. for example, a typical canine food composition may contain from about 10 to about 30% fat, about 22 to about 44% by weight protein and about 10% total dietary fiber. In another example, a typical feline food composition may contain from about 10 to about 30% by weight fat, and from about 30 to about 45% by weight protein. However, no specific ratios or percentages of these or other nutrients are required. A nutrient is any food constituent that helps support life. The following are examples of nutrients that have important roles in a companion animal's health:

TABLE 1

Typical Components of an Animal Diet

| | |
|---|---|
| Proteins | Main element of body tissues like muscles, blood, skin, organs, hair and nails. |
| Carbohydrates | Provide energy for the body's tissues. |
| Fats | Fats absorb, store and transport vitamins, moisturize skin and coat, make healthy pet food taste great and supply energy. |
| Water | The most critical nutrient for survival. |
| Vitamins | Assist in maintaining an animal's metabolism. |
| Minerals | Necessary to develop healthy skin and hair, proper skeletal support and development. Minerals are usually abundant in pet food ingredients. |

In various embodiments, a sulfur containing amino acid and manganese may be administered to the animal, preferably one in need of such administration, in at least one of many ways, such as oral, parenteral, and the like, although oral is preferred. In various embodiments, the sulfur containing amino acid and manganese may be administered in a wet or dry food composition, either incorporated therein or on the surface of any food component, such as, by spraying or precipitation thereon. In various embodiments, the sulfur containing amino acid and manganese may be present in the diet by way of a snack, a supplement, a treat or in the liquid portion of the diet such as water or another fluid. In various embodiments, the sulfur containing amino acid and manganese may be administered as a powder, solid or as a liquid including a gel. In various embodiments, the sulfur containing amino acid and manganese may be orally administered in a pharmaceutical dosage form such as a capsule, tablet, caplet, syringe, and the like and with such a dosage form, the sulfur containing amino acid and manganese may be present as a powder or a liquid such as a gel. Any of the usual pharmaceutical carriers may be employed such as water, glucose, sucrose and the like together with the sulfur containing amino acid and manganese. In various embodiments, the sulfur containing amino acid and manganese may be provided in liquids or in pharmaceutical dosage forms such as capsules, tablets, pills, liquids or even parenterally administered through syringe. Although exemplified together, the sulfur containing amino acid and manganese can be administered separately, that is one in a food composition and one in a liquid or a unit dose form, for example. Generally, the sulfur containing amino acid and manganese should be administered at least concomitantly, and preferably in the same carrier. An important aspect is that the animal be provided an effective amount of the sulfur containing amino acid and manganese to provide a positive cartilage effect. A positive cartilage effect may include one or more of increasing flexibility, repairing lesions, reducing inflammation, improving mobility, strengthening cartilage, reducing abnormalities, and/or preventing any of reduced flexibility and/or mobility, weakening and/or degrading cartilage, abnormalities and/or lesions, inflammation, or a cartilage affected condition, and the like. A preferred route of administration is oral and incorporated with a food suitable for consumption by an animal.

When administered in a food, the sulfur containing amino acid and manganese may be administered as a composition. Illustratively, such a composition can be a food composition, a supplement, a treat or a toy, it being noted that some, but not all, supplements, treats and toys are themselves food compositions. Food compositions are administered to the animal by feeding. Where the animal is a companion animal, a food composition is typically one that is nutritionally adapted for feeding to such an animal. A food composition so adapted is referred to herein as a "pet food". Pet foods can be more particularly adapted to the special nutritional needs of canines or felines, or to certain subpopulations thereof such as large-breed dogs, adult dogs or cats, senior dogs or cats, geriatric dogs or cats, etc.

In various embodiments, a food composition comprising sulfur containing amino acid and manganese provides a substantially nutritionally complete diet for the intended recipient animal. A "nutritionally complete diet" is a diet that includes sufficient nutrients for maintenance of normal health of a healthy animal on the diet.

In various embodiments, a food composition containing sulfur containing amino acid and manganese may be a supplement, i.e., a supplement used with another food composition to improve the nutritive balance or performance of the diet as a whole. Such supplements include compositions that are fed undiluted as a supplement to other foods, offered free choice with other parts of an animal's daily ration that are separately available to the animal, or diluted and mixed with an animal's regular food to produce a substantially nutritionally complete diet. Supplements can alternatively be in a form other than a food composition, for example in a pharmaceutical-like dosage form including, for example, powders, liquids, syrups, capsules, tablets, pills, etc.

In various embodiments, a supplement comprising an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, a supplement comprising an effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions. In various embodiments, a supplement comprising an effective amount of a sulfur containing amino acid and manganese further comprises an effective amount of at least one of glycine and proline.

In various embodiments, a food composition comprising sulfur containing amino acid and manganese may be a treat. Treats include, for example, compositions given to an animal as a reward or to entice the animal to eat during a non-meal time. Treats for dogs that are food compositions having at least some nutritional value include, for example, dog biscuits. Treats can alternatively be substantially non-nutritional (except to the extent that a sulfur containing amino acid and manganese therein can be considered nutrients). A composition comprising a sulfur containing amino acid and manganese can itself form a treat, be coated onto an existing treat, or both.

In various embodiments, a composition comprising a sulfur containing amino acid and manganese may be a toy adapted for oral use by an animal. Toys include, for example, chewable toys, such as artificial bones for dogs. A composition comprising a sulfur containing amino acid and manganese can form a coating on the surface of a toy or on the surface of a component of a toy, be incorporated partially or fully throughout the toy, or both. A wide range of suitable toys is currently marketed, including partially consumable toys (e.g., toys comprising plastic components) and fully consumable toys (e.g., rawhides and various artificial bones). Toys are available for human and non-human use, particularly for companion, farm, and zoo animal use, and more particularly for dog, cat, or bird use.

Various sulfur containing amino acids and their derivatives are applicable in various embodiments and these include but are not limited to D-methionine, L-methionine, DL-methionine, D-cysteine, L-cysteine, DL-cysteine, D-cystine, L-cystine, DL-cystine, S-adenosylmethionine, alpha and beta-hydroxy analogs of methionine, racemic mixtures thereof and the mixtures of the amino acids as described, and the like. In various embodiments, the sulfur containing amino acid can be provided per se to the animal or can be present naturally in dietary materials such as fish meal, corn gluten meal, poultry meal, casein, manganese methionine (a chelate) and the like.

The manganese may be supplied to the animal in various forms including, for example, manganous sulfate, manganous oxide, manganous dioxide, manganous carbonate, manganous chloride, manganese proteinate, manganese chelate, manganese monoxide, manganese methionine, and the like.

In various embodiments, the quantities of sulfur containing amino acid and manganese that should be employed in combination for bringing about the effect(s) can vary substantially. In various embodiments, a minimum amount of the sulfur containing amino acid is above about 1.2 wt. %, preferably above about 1.5 wt. % and more preferably above about 1.8 wt. %. In various embodiments, a minimum amount of manganese is above about 50 ppm, preferably above about 65 ppm and more preferably above about 100 ppm. In various embodiments, a specific amount of sulfur containing amino acid and manganese can be administered in the usual nutrient food ration on a daily basis or the same daily quantity can be administered to the animal in a treat or supplement on a daily basis. In various embodiments, a combination of these methods or any other dosing means can be employed as long as an effective quantity of the sulfur containing amino acid and manganese is provided. Maximum quantities of the sulfur containing amino acid and manganese is the highest amount that may be considered safe, for example, less than or equal to a LD50 of the sulfur containing amino acid or manganese. Examples of such quantities for the amino acid include not more than about 5.0 wt. %, 4.0 wt. % and 3.0 wt. % on the same basis as for the minimums. Examples of such quantities of manganese include not more than about 200 ppm, preferably not more than about 175 ppm and more preferably not more than about 150 ppm on the same basis as the minimums. In various embodiments, a composition comprising an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, a composition comprising an effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions. In various embodiments, a composition comprising an effective amount of a sulfur containing amino acid and manganese further comprises an effective amount of at least one of glycine and proline. In various embodiments, a minimum amount of glycine is about 1.4%, preferably about 1.6 wt. % and more preferably about 2.0 wt. %. In various embodiments, a minimum amount of proline is about 1.45 wt. %, preferably about 1.6 wt. % and more preferably, about 2.0 wt. %.

In various embodiments, a daily ration comprises an effective combination of a sulfur containing amino acid and manganese. In various embodiments, a daily ration comprises at least about 3.5 g/Mcal sulfur containing amino acid. In various embodiments, a daily ration comprises at least about 50 ppm/Mcal manganese. In some embodiments, a daily ration comprises at least about 3.5 g/Mcal sulfur containing acid and at least about 50 ppm/Mcal manganese. In various embodiments, a daily ration comprises an effective amount of a sulfur containing acid and manganese further comprises an effective amount of at least one of glycine and proline. In various embodiments, a daily ration comprises at least about 4.0 g/Mcal glycine. In various embodiments, a daily ration comprises at least about 4.0 g/Mcal proline. In various embodiments, the daily ration comprises at least about 4.0 g/Mcal glycine and at least about 4.0 g/Mcal proline. In various embodiments, a daily ration comprising an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, a daily ration comprising an effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions.

Various embodiments include a method for improving cartilage in an animal. In various embodiments, the method comprises feeding to the animal a food composition comprising a sulfur containing amino acid in an amount of at least about 1.2 wt. % and manganese in an amount of at least about 50 ppm on a dry matter basis per day. In various embodiments, the method comprises feeding to the animal a food composition comprising sulfur containing amino acid in an amount of at least about 1.8 wt. % and manganese in an amount of at least about 100 ppm on a dry matter basis per day. In various embodiments, the method comprises feeding to the animal a food composition comprising a sulfur containing amino acid in an amount from about 1.2 wt. % to about 3.6 wt. % and manganese in an amount from about 50 ppm to about 200 ppm on a dry matter basis per day. In various embodiments, the method comprises feeding to the animal a food composition comprising an effective amount of a sulfur containing amino acid and manganese further comprises an effective amount of at least one of glycine and proline. In various embodiments, a minimum amount of glycine is about 1.4%, preferably about 1.6 wt. % and more preferably about 2.0 wt. %. In various embodiments, the food composition comprises an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, the food composition comprising an effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions.

In various embodiments, the method comprises feeding to the animal a daily ration comprising an effective amount of a sulfur containing amino acid and manganese. In various embodiments, the effective amount of a sulfur containing amino acid and manganese may be added to the daily ration by a compounder or a manufacturer at a site or by an animal's caregiver as a supplement. In various embodiments, a daily ration comprises at least about 3.5 g/Mcal of a sulfur containing amino acid. In various embodiments, a daily ration comprises at least about 50 ppm/Mcal manganese. In some embodiments, a daily ration comprises at least about 3.5 g/Mcal of a sulfur containing acid and at least about 50 ppm/Mcal manganese. In various embodiments, the daily ration comprises an effective amount of a sulfur containing acid and manganese further comprises an effective amount of at least one of glycine and proline. In various embodiments, the daily ration comprises at least about 4.0 g/Mcal glycine. In various embodiments, the daily ration comprises at least about 4.0 g/Mcal proline. In various embodiments, the daily ration comprises at least about 4.0 g/Mcal glycine and at least about 4.0 g/Mcal proline. In various embodiments, the daily ration comprises an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, the daily ration comprising an effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions.

In various embodiments, a daily ration comprises increased sulfur containing amino acid and manganese that improves the health of the companion animal's joints. In various embodiments, the sulfur containing amino acid and manganese is added to an animal's food. In various embodiments, the sulfur containing amino acid and manganese may be added to the animal's food by a compounder, or manufacturer at a site, or by an animal's caretaker prior to feeding the animal. In such embodiments, the manganese and sulfur containing amino acid may be added during the processing of an animal food that is then packaged and made available to consumers. Such processing may include extrusion, canning, baking, and the like or any other method or process of producing pet foods that is known in the art. In various embodiments, the sulfur containing amino acid and manganese may be contributed by a natural source like an animal or plant component or the sulfur containing amino acid and manganese may be contributed by a synthetically derived source or the sulfur containing amino acid and manganese may be contributed by a mixture of natural and synthetic sources.

In preparing an illustrative canned or wet food composition, ground animal and poultry proteinaceous tissues are mixed with other ingredients, including fish oils, cereal grains, other nutritionally balancing ingredients, special-purpose additives (e.g., vitamin and mineral mixtures, inorganic salts, cellulose and beet pulp, bulking agents, and the like); and water in an amount sufficient for processing is also added. These ingredients can be mixed in a vessel suitable for heating while blending the components. Heating of the mixture may be affected in any suitable manner, such as, for example, by direct steam injection or by using a vessel fitted with a heat exchanger. Following addition of the last ingredient, the mixture is heated to a temperature range of about 50° F. to about 212° F., for example about 70° F. to about 140° F. Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

Food compositions can alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

Treats can be prepared by, for example, an extrusion or baking process similar to those described above for a dry food composition. Other processes also may be used to either coat a composition comprising sulfur containing amino acid and manganese on the exterior of an existing treat form, or inject it into an existing treat form. Toys useful herein can illustratively be prepared by coating an existing toy with a composition comprising a sulfur containing amino acid and manganese.

In various embodiments, an effective amount of a sulfur containing amino acid and manganese may be administered to an animal. In various embodiments, the sulfur containing amino acid and manganese may be in a capsule form to be fed to the animal. In various embodiments, the effective amount of a sulfur containing amino acid and manganese may be in a powder or in a crystalline that may be added to the animal's food or fed directly to the animal. In various embodiments, the sulfur containing amino acid and manganese may be a supplement that is added to an animal's food or daily ration. Such supplements include compositions that are fed undiluted as a supplement to other foods, offered free choice with other parts of an animal's daily ration that are separately available to the animal, or diluted and mixed with an animal's regular food to produce a substantially nutritionally complete diet. Supplements can alternatively be in a form other than a food composition, for example in a pharmaceutical-like dosage form including, for example, powders, liquids, syrups, capsules, tablets, pills, etc.

In various embodiments, the supplement comprising an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, a supplement comprising the effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions. In various embodiments, a supplement comprising the effective amount of a sulfur containing amino acid and manganese further comprises an effective amount of at least one of glycine and proline. In various embodiments, an animal food composition comprises an effective amount of a sulfur containing amino acid and manganese and other needed nutritional components. In various embodiments, the effective amount of a sulfur containing amino acid and manganese may be administered to an animal via a syringe. In various embodiments, a dosage comprises at least about 3.5 g/Mcal of sulfur containing amino acid. In various embodiments, a dosage comprises at least about 50 ppm/Mcal manganese. In some embodiments, a dosage comprises at least about 3.5 g/Mcal sulfur containing amino acid and at least about 50 ppm/Mcal manganese.

In various embodiments, a dosage comprising an effective amount of a sulfur containing amino acid and manganese further comprises an effective amount of at least one of glycine and proline. In some embodiments, the dosage comprises at least about 4.0 g/Mcal glycine. In various embodiments, the dosage comprises at least about 4.0 g/Mcal proline. In some embodiments, the dosage comprises at least about 4.0 g/Mcal glycine and at least about 4.0 g/Mcal proline. In various embodiments, a dosage comprising an effective amount of a sulfur containing amino acid and manganese further comprises an effective amount of at least one substance selected from the group consisting of glucosamine, chondroitin, chondroitin sulfate, MSM, creatine, antioxidants, *Perna canaliculata*, omega-3 fatty acids, omega-6 fatty acids and mixtures thereof. In various embodiments, a dosage comprising an effective amount of the sulfur containing amino acid and manganese further comprises an effective amount of at least one substance selected from the group consisting of aspirin, anti-inflammatories such as ibuprofen, COX-2 inhibitors, and other medicinal and pharmaceutical compositions.

One measure of cartilage health is the quantity of abnormalities visually observed on the cartilage. Other ways of observing cartilage abnormalities include MRI, computerized tomography and radiography. The higher the quantity of abnormalities, the further the overall joint is weakened that makes it more susceptible to a condition or exacerbates an existing condition. These conditions include arthritis (both osteo and rheumatoid), osteochondrosis, degenerative joint disease, synovitis, bacterial purulent arthritis, osteoarthropathia and psoriatica among others. The visualized cartilage abnormalities include lesions in general, erosions, and abnormal growths.

In another aspect, the present invention provides a means for communicating information about or instructions for improving cartilage abnormalities and preventing cartilage degradation in an animal. The communicating means comprises a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for administering the compositions and using the methods of he present invention, (2) details about the side effects, if any, caused by using the present invention, alone or in combination with other drugs, and (3) contact information for patients to use if they have a question about the invention and its use. Useful instructions include dosages, administration amounts and frequency, and administration routes. The communication means is useful for instructing on the benefits of using the present invention and communicating the approved methods for using the invention.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use. The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

In a further aspect, the present invention provides a kit comprising in separate containers in a single package: (1) at least one sulfur-containing amino acid or manganese and (2) at least one sulfur-containing amino acid (when manganese is used alone in (1)); manganese (when at least one sulfur-containing amino acid is used alone in (1)); a food suitable for consumption by an animal; at least one substance selected from the group consisting of glucosamine, chondroitin, chondroitin sulfate, MSM, creatine, antioxidants, *Perna canaliculata*, omega-3 fatty acids, omega-6 fatty acids, and mixtures thereof; and a means for communicating information about or instructions for managing cartilage affecting conditions, increasing cartilage flexibility, increasing cartilage strength, or preventing cartilage degradation in an animal. In other embodiments, the kits further comprise one or more drugs useful for managing a cartilage affecting condition, increasing cartilage flexibility, increasing cartilage strength, or preventing cartilage degradation, e.g., an effective amount of at least one substance selected from the group consisting of aspirin, anti-inflammatory compounds such as ibuprofen, COX-2 inhibitors, and an effective amount of at least one of a sulfur containing amino acid and manganese.

The kit components are typically in a separate package, in or on the package with one of the other kit components, or in a virtual package, as appropriate for the type of kit component. When the kit comprises a virtual package, the kit is limited to the instructions in a virtual environment in combination with one or more of the other physical kit components.

EXAMPLE 1

Growing pigs (80 experimental units) are used as test model to determine the effect of methionine and manganese on cartilage abnormalities. The pigs are initially about 35 kg. Each pig was individually housed in 5.2 ft$^2$ pens with ad libitum access to food and water. The pigs are fed test foods for a period of 60 days to an approximate final weight of about 130 kg.

At the point of meat fabrication, the distal aspect of the right femur bone is collected and evaluated for gross lesions as well as histopathology characterizations. The distal aspect of the right femur bone is preserved in formaldehyde and stored at room temperature for gross observation. The joints are evaluated for the total number of lesions present on the joint surface (including clinical lesions, cartilage erosions and abnormal growth patterns). Gross lesions are confirmed by histopathology characterization. Tissue sections are taken from the ventral weight baring aspects of the medial femoral condyle. Measures are evaluated on 2× and 10×photomicrographs to determine cell counts and to confirm pathological damage of the cartilage into the subchondral bone.

TABLE 2

Composition of Experimental Foods

|  | Control | Sample 1 | Sample 2 | Sample 3 |
|---|---|---|---|---|
| Corn | 71.00 | 78.50 | 71.00 | 71.00 |
| Soybean Meal | 18.70 | 3.35 | 18.70 | 18.70 |
| Corn Starch | 3.78 | 3.00 | 2.52 | 2.48 |
| Ch White Grease | 3.00 | 1.00 | 3.00 | 3.00 |
| Dical | 1.97 | 1.13 | 1.98 | 2.03 |
| Limestone | 0.62 | 0.28 | 0.77 | 0.74 |
| Salt | 0.43 | 0.31 | 0.55 | 0.55 |
| L-lysine | 0.15 | 0.08 | 0.15 | 0.15 |
| Vitamin premix | 0.10 | 0.10 | 0.10 | 0.10 |
| Choline | 0.10 | 0.10 | 0.10 | 0.10 |
| TM premix | 0.10 | 0.10 | 0.10 | 0.10 |
| Mn sulfate |  | 0.02 |  | 0.02 |
| Tryptophan |  | 0.03 |  |  |
| Poultry Meal |  | 12.00 |  |  |
| DL-methionine | 0.04 |  | 1.03 | 1.03 |
| Total 100% DM basis | 100 | 100 | 100 | 100 |
| ME, Kcal/kg | 3604 | 3634 | 3604 | 3604 |
| Ca, % | 0.86 | 0.85 | 0.86 | 0.86 |
| P, % | 0.74 | 0.74 | 0.74 | 0.74 |
| Na, % | 0.22 | 0.22 | 0.22 | 0.22 |
| Lys, % | 0.97 | 0.96 | 0.97 | 0.97 |
| TSAA, % | 0.58 | 0.60 | 1.71 | 1.71 |
| Trp, % | 0.20 | 0.20 | 0.20 | 0.20 |
| Thr, % | 0.66 | 0.70 | 0.66 | 0.66 |
| Iso, % | 0.65 | 0.65 | 0.65 | 0.65 |
| Sulfur, ppm | 1664 | 2229 | 4147 | 4238 |
| Manganese, ppm | 41.3 | 107.8 | 41.2 | 127.4 |

TABLE 3

Analytical Analyses of Experimental Foods - Lot 1

|  | Control | Sample 1 | Sample 2 | Sample 3 |
|---|---|---|---|---|
| Crude protein | 17.32 | 18.34 | 16.63 | 16.93 |
| Fat | 7.76 | 7.58 | 7.46 | 7.42 |

TABLE 3-continued

Analytical Analyses of Experimental Foods - Lot 1

|  | Control | Sample 1 | Sample 2 | Sample 3 |
|---|---|---|---|---|
| Fiber | 2.05 | 1.73 | 2.23 | 2.37 |
| Methionine + Cystine | 0.70 | 0.72 | 1.51 | 1.78 |
| Manganese | 46.4 | 81.2 | 43.4 | 110.0 |

TABLE 4

Analytical Analyses of Experimental Foods - Lot 2

|  | Control | Sample 1 | Sample 2 | Sample 3 |
|---|---|---|---|---|
| Crude protein | 17.38 | 18.43 | 19.30 | 17.94 |
| Fat | 6.83 | 7.89 | 7.54 | 7.46 |
| Fiber | 2.91 | 1.82 | 2.47 | 2.22 |
| Methionine + Cystine | 0.68 | 0.78 | 1.61 | 1.56 |
| Manganese | 41.8 | 96.8 | 42.2 | 110.1 |

TABLE 5

Effect of Nutrients on Cartilage Abnormalities

|  | Control | Sample 1 | Sample 2 | Sample 3 |
|---|---|---|---|---|
| Total lesions | 2.38 | 2.25 | 1.38 | 0.88 |

As shown by the data, a combination of increased sulfur containing amino acid methionine and cystine and manganese statistically reduces the number of visually observed abnormalities (for example, lesions and erosions) abnormalities of the cartilage, as shown by Sample 3. The effect of the combination was greater than that of methionine and cystine alone and that manganese alone had substantially no effect. Sample 1 is high in manganese but approximately the same in sulfur containing amino acid as control. Sample 2 is high in sulfur containing amino acid but approximately the same in manganese as the control.

EXAMPLE 2

Growing pigs (80 experimental units) are used as test model to determine the effect of methionine and manganese on cartilage abnormalities. The pigs are initially about 35 kg. Each pig was individually housed in 5.2 ft² pens with ad libitum access to food and water. The pigs are fed test foods for a period of 90 days to an approximate final weight of about 130 kg.

TABLE 6

Effect of GAGS, Methionine, Manganese, Glycine and Proline on Cartilage Degradation in Growing Pigs Effect of Cartilage Building Blocks on Serum Matrix Metalloproteinase and Inhibitor Concentrations

| GAGS | no | yes | no | no | no | no | no | yes |  |
|---|---|---|---|---|---|---|---|---|---|
| Methionine | 0.30 | 0.34 | 1.43 | 0.30 | 0.30 | 0.30 | 1.43 | 1.38 |  |
| Manganese | 41 | 108 | 128 | 41 | 41 | 41 | 128 | 127 |  |
| Glycine | 0.79 | 1.29 | 0.78 | 1.68 | 1.68 | 2.58 | 1.68 | 1.68 |  |
| Proline | 1.14 | 1.29 | 1.14 | 1.69 | 2.23 | 1.69 | 1.69 | 1.68 | CV |
| Enzyme, mg/dl |  |  |  |  |  |  |  |  |  |
| MMP-3 | 4.65 | 3.98 | 5.43 | 6.61*** | 5.15 | 4.61 | 4.97 | 4.50 | 45.67 |
| MMP-8 |  |  |  |  |  |  |  |  |  |
| MMP-13 | 2.29 | 0.34* | 0.28* | 1.38 | 0.49* | 0.53* | 0.62*** | 0.70*** | 238.86 |

Effect of Cartilage Building Blocks on Collagen Synthesis

| GAGS | no | yes | No | no | no | no | no | yes |
|---|---|---|---|---|---|---|---|---|
| Methionine | 0.30 | 0.34 | 1.43 | 0.30 | 0.30 | 0.30 | 1.43 | 1.38 |

TABLE 6-continued

Effect of GAGS, Methionine, Manganese, Glycine and Proline on Cartilage Degradation in Growing Pigs

| Manganese | 41 | 108 | 128 | 41 | 41 | 41 | 128 | 127 | |
|---|---|---|---|---|---|---|---|---|---|
| Glycine | 0.79 | 1.29 | 0.78 | 1.68 | 1.68 | 2.58 | 1.68 | 1.68 | |
| Proline | 1.14 | 1.29 | 1.14 | 1.69 | 2.23 | 1.69 | 1.69 | 1.68 | CV |
| Item | | | | | | | | | |
| Type II Collagen | 120.43 | 111.62 | 89.76* | 105.49 | 88.66* | 118.38 | 91.34* | 103.7 | 29.3 |
| CP2 | 730.78 | 764.03 | 687.02 | 733.99 | 704.09 | 726.14 | 724.31 | 707.08 | 15.5 |

Effect of Cartilage Building Blocks on Cartilage Gross and Histological Pathology

| GAGS | no | yes | No | no | no | no | no | yes | |
|---|---|---|---|---|---|---|---|---|---|
| Methionine | 0.30 | 0.34 | 1.43 | 0.30 | 0.30 | 0.30 | 1.43 | 1.38 | |
| Manganese | 41 | 108 | 128 | 41 | 41 | 41 | 128 | 127 | |
| Glycine | 0.79 | 1.29 | 0.78 | 1.68 | 1.68 | 2.58 | 1.68 | 1.68 | |
| Proline | 1.14 | 1.29 | 1.14 | 1.69 | 2.23 | 1.69 | 1.69 | 1.68 | CV |
| Item | | | | | | | | | |
| Gross Lesions, Number | 2.38 | 1.29 | 1.86 | 1.50 | 1.00* | 1.75 | 1.17*** | 1.89 | 98.97 |
| Thickness, mm | 1.90 | 1.94 | 2.01 | 1.94 | 2.10 | 1.87 | 2.01 | 1.93 | 12.10 |

*Control vs Treatment, (P < .05)
**Control vs Treatment, (P < .01)
***Control vs Treatment, (P < .10)

These data show that cartilage degradation is reduced as evidenced by reduced MMP-13 activity and reduced Type II collagen synthesis (less cartilage repair). The result is reduced cartilage lesions.

Serum samples are harvested at the end of the 90 day period to determine matrix metalloproteinase activity (MMP-13) and Type 2 collagen synthesis activity. As shown by the above data, a combination of increased sulfur containing amino acid and manganese improves cartilage as shown by improvements in the enzyme MMP-13 and the Type 2 collagen synthesis activity.

EXAMPLE 3

Cats from two months to eight months of age were evaluated for cartilage health. The cats were divided into groups and Group 1 was fed a control food, Group 2 was fed a food enriched with glycine and proline, Group 3 was fed a food enriched with methionine and manganese, and Group 4 was fed a food enriched with glycine, proline, methionine, and manganese. Table 7 illustrates data for different components measured in the serum of the cats in the study.

TABLE 7

Effects of Amino Acids and Manganese on Cartilage Health in Felines

| Item | Control | TSAA Mn | Glycine Proline | Gly/Pro TSAA/Mn |
|---|---|---|---|---|
| Glycine/Mcal, g/Mcal | 5.8 | 5.8 | 7.6 | 7.7 |
| Proline/Mcal, g/Mcal | 5.1 | 5.0 | 6.6 | 6.6 |
| Methionine/Mcal, g/Mcal | 1.6 | 3.3 | 1.5 | 3.3 |
| Manganese/Mcal, ppm/Mcal | 4.11 | 33.13 | 4.13 | 33.09 |
| D-pyrodinoline | 6.87 | 5.60* | 6.53 | 6.72 |
| Pyrodinoline | 3.85 | 3.51 | 3.65 | 3.38** |
| NTx | 10.66 | 10.35 | 11.46 | 11.7 |
| CTx | 13.11 | 12.67 | 13.02 | 10.54*** |
| Osteocalcin | 0.88 | 1.62** | 1.92*** | 1.51 |
| Bone specific alkaline phosphatase | 37.66 | 37.42 | 39.79 | 39.25 |

*Difference between treatment and control, P < .10
**Difference between treatment and control, P < .17
***Difference between treatment and control, P < .05

EXAMPLE 4

The data in Table 8 illustrates results from the study that show cartilage damage can be reduced in puppies fed glycine, proline, methionine and manganese.

TABLE 8

Effect of Amino Acids and Manganese on Cartilage Health in Canines

| Item | Control | Glycine/Proline TSAA/Mn | P-value |
|---|---|---|---|
| Glycine/Mcal, g/Mcal | 5.1 | 6.0 | |
| Proline/Mcal, g/Mcal | 4.2 | 5.0 | |
| Methionine/Mcal, g/Mcal | 1.3 | 3.5 | |
| Manganese/Mcal, ppm/Mcal | 7.70 | 33.54 | |
| CTx | | | |
| Initial | 17.78 | 14.84 | 0.31 |
| Final | 9.43 | 7.9 | 0.10 |
| Change | −8.82 | −6.95 | |
| Change from beginning to end P value | 0.01 | 0.01 | |
| Type II Collagen Synthesis | | | |
| Initial | 458 | 516 | 0.07 |
| Final | 445 | 409 | 0.38 |
| Change | −13.5 | −107 | 0.09 |
| Change from beginning to end P value | 0.72 | 0.01 | |
| MMP-13 | | | |
| Initial | 0.6 | 0.44 | 0.47 |
| Final | 0.32 | 0.51 | 0.18 |
| Change | −0.28 | 0.08 | 0.17 |
| Change from beginning to end P value | 0.14 | 0.65 | |

The words "comprise", "comprises", and "comprising" are to be interpreted inclusively rather than exclusively. Except where stated otherwise, all percentages recited herein are weight percentages on a dry matter basis. The phrase "dry matter basis" means the component concentration in the composition after any moisture in the composition is removed.

The examples and other embodiments described herein are exemplary and are not intended to be limiting in describing the full scope of apparatus, systems, compositions, materials, and methods of these embodiments. Equivalent changes, modifications, variations in specific embodiments, apparatus, systems, compositions, materials and methods may be made within the scope of the various embodiments with substantially similar results. Such changes, modifications or variations are not to be regarded as a departure from the spirit and scope of the various embodiments.

What is claimed is:

1. A method for improving cartilage abnormalities in a companion animal comprising administering to a companion animal in need thereof a pet food composition comprising (i) 1.2-5% by weight of at least one sulfur-containing amino acid selected from the group consisting of D-methionine, L-methionine, DL-methionine, D-cysteine, L-cysteine, DL-cysteine, D-cystine, L-cystine, DL-cystine, and mixtures thereof; (ii) 50-200 ppm manganese; (iii) a source of protein; (iv) a source of fat; (v) a source of fiber; and (vi) at least one of glycine and proline, wherein the glycine is in an amount of at least 4.0 g/Mcal and the proline is in an amount of at least 4.0 g/Mcal.

2. The method of claim 1 wherein the animal is a canine or a feline.

3. The method of claim 1 wherein the sulfur containing amino acid, manganese, source of protein, source of fat, source of fiber and at least one of glycine and proline are provided in a food.

4. The method of claim 1 wherein the cartilage abnormality is selected from the group consisting of osteoarthritis, rheumatoid arthritis, osteochondrosis, degenerative joint disease, synovitis, bacterial purulent arthritis, and osteoarthropathia psoriatica.

5. The method of claim 1 further comprising administering to the animal an effective amount of at least one substance selected from the group consisting of glucosamine, chondroitin, chondroitin sulfate, MSM, creatine, antioxidants, Perna canaliculata, omega-3 fatty acids, omega-6 fatty acids, and mixtures thereof.

6. A method according to claim 1, wherein the composition comprises 1.2-3% of the at least one sulfur containing amino acid and 50-150 ppm manganese.

7. A method according to claim 1, wherein the composition comprises 1.5-3% of the at least one sulfur containing amino acid and 50-150 ppm manganese.

8. A method according to claim 1, wherein the composition comprises 1.8-3% of the at least one sulfur containing amino acid and 100-200 ppm manganese.

9. A method according to claim 1, wherein the composition comprises 1.8-3% of the at least one sulfur containing amino acid and 100-150 ppm manganese.

10. A method for treating cartilage degradation in a companion animal comprising administering to a companion animal in need thereof a pet food composition comprising (i) 1.2-5.% by weight of at least one sulfur-containing amino acid selected from the group consisting of D-methionine, L-methionine, DL-methionine, D-cysteine, L-cysteine, DL-cysteine, D-cystine, L-cystine, DL-cystine, and mixtures thereof; (ii) 50-200 ppm manganese; (iii) a source of protein; (iv) a source of fat; (v) a source of fiber; and (vi) at least one of glycine and proline, wherein the glycine is in an amount of at least 4.0 g/Mcal and the proline is in an amount of at least 4.0 g/Mcal.

11. The method of claim 10 wherein the animal is a canine or a feline.

12. The method of claim 10 wherein the sulfur containing amino acid, manganese, source of protein, source of fat, source of fiber and at least one of glycine and proline are provided in a food.

13. The method of claim 10 wherein the cartilage degradation is caused by a cartilage abnormality selected from the group consisting of osteoarthritis, rheumatoid arthritis, osteochondrosis, degenerative joint disease, synovitis, bacterial purulent arthritis, and osteoarthropathia psoriatica.

14. The method of claim 10 further comprising administering to the animal an effective amount of at least one substance selected from the group consisting of glucosamine, chondroitin, chondroitin sulfate, MSM, creatine, antioxidants, Perna canaliculata, omega-3 fatty acids, omega-6 fatty acids and mixtures thereof.

15. A method according to claim 10, wherein the composition comprises 1.2-3% of the at least one sulfur containing amino acid and 50-150 ppm manganese.

16. A method according to claim 10, wherein the composition comprises 1.5-3% of the at least one sulfur containing amino acid and 50-150 ppm manganese.

17. A method according to claim 10, wherein the composition comprises 1.8-3% of the at least one sulfur containing amino acid and 100-200 ppm manganese.

18. A method according to claim 10, wherein the composition comprising 1.2-3% of the at least one sulfur containing amino acid and 100-150 ppm manganese.

19. A composition suitable for decreasing cartilage abnormalities or treating cartilage degradation in a companion animal in need thereof comprising administering a pet food composition comprising (i) 1.2-5% by weight of at least one sulfur-containing amino acid selected from the group consisting of D-methionine, L-methionine, DL-methionine, D-cysteine, L-cysteine, DL-cysteine, D-cystine, L-cystine, DL-cystine, and mixtures thereof; (ii) 50-200 ppm manganese; (iii) a source of protein; (iv) a source of fat; (v) a source of fiber; and (vi) at least one of glycine and proline at least one of glycine and proline, wherein the glycine is in an amount of at least 4.0 g/Mcal and the proline is in an amount of at least 4.0 g/Mcal.

20. The composition of claim 19 further comprising at least one substance selected from the group consisting of glucosamine, chondroitin, chondroitin sulfate, MSM, creatine, antioxidants, Perna canaliculata, omega-3 fatty acids, omega-6 fatty acids and mixtures thereof.

21. The composition of claim 19 further comprising a food suitable for consumption by an animal.

22. A method for improving cartilage abnormalities in a cat comprising administering to a cat in need thereof a pet food composition comprising (i)1.2-5% by weight of at least one sulfur-containing amino acid selected from the group consisting of D-methionine, L-methionine, DL-methionine, D-cysteine, L-cysteine, DL-cysteine, D-cystine, L-cystine, DL-cystine, and mixtures thereof; (ii) 50-200 ppm manganese; (iii) a source of protein; (iv) a source of fat; (v) a source of fiber; and (vi) at least one of glycine and proline, wherein the glycine is in an amount of at least 4.0 g/Mcal and the proline is in an amount of at least 4.0 g/Mcal.

23. A method according to claim 22, wherein the cartilage abnormality is selected from the group consisting of osteoarthritis, rheumatoid arthritis, osteochondrosis, degenerative joint disease, synovitis, bacterial purulent arthritis, and osteoarthropathia psoriatica.

24. A method according to claim 22, further comprising administering to the cat an effective amount of at least one substance selected from the group consisting of glucosamine, chondroitin, chondroitin sulfate, MSM, creatine, antioxidants, Perna canaliculata, omega-3 fatty acids, omega-6 fatty acids, and mixtures thereof.

25. A method according to claim 22, wherein the composition comprises 1.2-3% of the at least one sulfur containing amino acid and 50-150 ppm manganese.

26. A method according to claim 22, wherein the composition comprises 1.5-3% of the at least one sulfur containing amino acid and 50-150 ppm manganese.

27. A method according to claim 22, wherein the composition comprises 1.8-3% of the at least one sulfur containing amino acid and 100-200 ppm manganese.

28. A method according to claim 22, wherein the composition comprises 1.8-3% of the at least one sulfur containing amino acid and 100-150 ppm manganese.

\* \* \* \* \*